(12) United States Patent
Imhof et al.

(10) Patent No.: US 9,314,564 B2
(45) Date of Patent: Apr. 19, 2016

(54) PUMP CONTROLLER THAT CHECKS OPERATIONAL STATE OF INSULIN PUMP FOR CONTROLLING THE INSULIN PUMP

(71) Applicants: Roche Diagnostics International AG, Rotkreuz (CH); Roche Diagnostics Operations, Inc., Indianapolis, IN (US)

(72) Inventors: Erich Imhof, Utzenstorf (CH); Guido Konrad, Bern (CH); James R. Long, Fishers, IN (US); Phillip E. Pash, Indianapolis, IN (US); Robert E. Reinke, Indianapolis, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 720 days.

(21) Appl. No.: 13/680,878

(22) Filed: Nov. 19, 2012

(65) Prior Publication Data

US 2014/0142535 A1    May 22, 2014

(51) Int. Cl.
*A61M 5/142* (2006.01)
*G06F 19/00* (2011.01)

(52) U.S. Cl.
CPC .......... *A61M 5/142* (2013.01); *A61M 5/14244* (2013.01); *G06F 19/3468* (2013.01); *A61M 2205/3561* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2209/01* (2013.01)

(58) Field of Classification Search
CPC .......... A61M 5/142; A61M 5/14244; A61M 2205/3592; A61M 2209/01; A61M 2205/3576; A61M 2205/502; A61M 2205/3584; A61M 2205/50; A61M 2205/3561; G06F 19/3468
See application file for complete search history.

(56) References Cited

U.S. PATENT DOCUMENTS

| | | | |
|---|---|---|---|
| 5,741,211 A * | 4/1998 | Renirie et al. | 600/300 |
| 7,942,844 B2 * | 5/2011 | Moberg et al. | 604/65 |
| 8,118,770 B2 | 2/2012 | Galley et al. | |
| 2004/0122530 A1 | 6/2004 | Hansen et al. | |
| 2007/0060796 A1 * | 3/2007 | Kim | 600/300 |
| 2008/0183060 A1 * | 7/2008 | Steil et al. | 600/365 |
| 2008/0300572 A1 | 12/2008 | Rankers et al. | |
| 2008/0312512 A1 * | 12/2008 | Brukalo et al. | 600/300 |
| 2009/0069745 A1 * | 3/2009 | Estes et al. | 604/67 |
| 2009/0177154 A1 * | 7/2009 | Blomquist | 604/131 |

(Continued)

FOREIGN PATENT DOCUMENTS

| | | | |
|---|---|---|---|
| EP | 1338295 A1 | 8/2003 | |
| EP | 1839694 A1 | 10/2007 | |
| WO | WO-2007000427 A1 | 1/2007 | |

*Primary Examiner* — Ramesh Patel
(74) *Attorney, Agent, or Firm* — Harness, Dickey (57) ABSTRACT

A computer-implemented method of operating a diabetes treatment system that includes an insulin pump and a pump controlling device is disclosed. The method includes receiving, by the device, a request for the pump to perform an operation that is dependent on a specified state of the pump. The method also includes requesting, by the device, a current state of the pump from the pump. Moreover, the method includes receiving, by the device, the current state of the pump. Also, the method includes determining, by the device, whether the current state of the pump matches to the specified state of the pump. Additionally, the method includes sending, by the device to the pump, a command to perform the operation in response to a determination that the current state of the pump matches the specified state of the pump.

18 Claims, 5 Drawing Sheets

(56) References Cited

U.S. PATENT DOCUMENTS

| | | |
|---|---|---|
| 2009/0227855 A1* | 9/2009 | Hill et al. .................. 600/365 |
| 2010/0064257 A1 | 3/2010 | Buck et al. |
| 2010/0125241 A1* | 5/2010 | Prud'homme et al. ......... 604/65 |
| 2010/0160860 A1 | 6/2010 | Celentano et al. |
| 2011/0047499 A1 | 2/2011 | Mandro et al. |
| 2011/0124996 A1* | 5/2011 | Reinke et al. ............... 600/365 |
| 2012/0172802 A1* | 7/2012 | Blomquist .................. 604/151 |
| 2012/0245556 A1* | 9/2012 | Kovatchev et al. .......... 604/504 |
| 2013/0041342 A1* | 2/2013 | Bernini et al. .............. 604/500 |

* cited by examiner

PUMP CONTROLLER THAT CHECKS OPERATIONAL STATE OF INSULIN PUMP FOR CONTROLLING THE INSULIN PUMP

FIELD

The present disclosure relates to a pump controller and, more particularly, to a pump controller that checks the operational state of the insulin pump as a part of controlling the insulin pump.

BACKGROUND

Diabetes mellitus, often referred to as diabetes, is a chronic condition in which a person has elevated blood glucose levels that result from defects in the body's ability to produce and/or use insulin. Diabetes can be treated by injecting predetermined dosages of insulin to the patient to control the level of glucose in the bloodstream. For instance, some diabetes patients rely on an insulin pump to deliver the predetermined dosages to the patient.

The insulin pump can closely imitate a normally functioning pancreas by releasing multiple small doses of insulin each day into the body through an infusion set to regulate blood glucose levels. The dosage delivery rate of these small doses (i.e., the basal rate) can vary from user to user. Also, even for a particular user, the basal rate can change throughout the day, and the basal rate can depend upon various factors (e.g., the user's metabolism, physical health, stress levels, amount of exercise, etc.).

Insulin pumps can also deliver (either automatically or selectively) bolus doses of insulin. These bolus doses can be delivered before meals or snacks to compensate for the caloric intake. Also, bolus dosages can be delivered to correct high blood glucose levels. Moreover, the pump can be configured to deliver multiple types of bolus dosages (e.g., a "standard bolus," an "extended bolus," a "combination bolus/multiwave bolus," and a "super bolus"). These dosages can be adjusted according to the patient's particular physiology, eating habits, etc.

Many insulin pumps are programmable so that the basal and bolus dosages can be tailored to the particular user. Some pumps are also capable of communicating with a separate computing device and are compatible with software applications that may be executed on the computing device.

SUMMARY

This section provides a general summary of the disclosure, and is not a comprehensive disclosure of its full scope or all of its features.

A computer-implemented method of operating a diabetes treatment system that includes an insulin pump and a pump controlling device is disclosed. The pump controlling device is operable to communicate with and control the insulin pump. The method includes receiving, by the pump controlling device, a request for the insulin pump to perform an operation that is dependent on a specified state of the pump. The method also includes requesting, by the pump controlling device, a current state of the insulin pump from the insulin pump. Moreover, the method includes receiving, by the pump controlling device from the insulin pump, the current state of the insulin pump. Also, the method includes determining, by the pump controlling device, whether the current state of the insulin pump matches to the specified state of the insulin pump. Additionally, the method includes sending, by the pump controlling device to the insulin pump, a command to perform the operation in response to a determination that the current state of the insulin pump matches the specified state of the insulin pump.

In some embodiments, the method can also include performing, by the pump controlling device, a corrective action intended to change the current state of the insulin pump. Performing the corrective action can occur in response to a determination that the current state of the insulin pump does not match the specified state of the insulin pump. The corrective action can include sending, by the pump controlling device to the insulin pump, a command to change the current state of the insulin pump to the specified state of the pump.

Moreover, in some embodiments, the insulin pump has a run state and at least one of a pause state and a stop state. The request to perform an operation can be a request for the insulin pump to start insulin delivery, wherein starting insulin delivery is dependent on the insulin pump currently being in the at least one of the pause state and the stop state. Sending the command to start insulin delivery can occur in response to a determination that the current state of the insulin pump is the at least one of the pause state and the stop state.

Additionally, in some embodiments, the insulin pump can have a run state and at least one of a pause state and a stop state. The request to perform an operation can be a request for the insulin pump to activate a temporary basal rate of delivery of insulin, and activating the temporary basal rate can be dependent on the insulin pump currently being in a run state. Sending the command to activate the temporary basal rate can occur in response to a determination that the current state of the insulin pump is in the run state.

Furthermore, the method can include requesting, by the pump controlling device from the insulin pump, an execution result of sending the command to perform the operation. Also, the method can include outputting, by the pump controlling device, a message that conveys the execution result. Moreover, outputting the message can include visually displaying the message on a display that is included on the pump controlling device.

Moreover, a diabetes treatment system is disclosed that includes an insulin pump operable to selectively deliver insulin to a patient. The system also includes a pump controlling device with a communications component that is operable to provide two-way communication between the insulin pump and the pump controlling device. The pump controlling device also includes an input component configured to receive a request for the insulin pump to perform an operation that is dependent on a specified state of the insulin pump. The pump controlling device also includes a processor that is operable to request a current state of the insulin pump from the insulin pump via the communications component. The processor is also operable to receive the current state of the insulin pump from the insulin pump. The processor is further operable to determine whether the current state of the insulin pump matches to the specified state of the insulin pump. Also, the processor is also operable to send a command via the communications component to the insulin pump to perform the operation in response to a determination that the current state of the insulin pump matches the specified state of the insulin pump.

Still further, a pump controlling device is disclosed that is operable to control an insulin pump. The pump controlling device includes a communications component that is operable to provide two-way communication with the insulin pump. The pump controlling device further includes an input component configured to receive a request for the insulin pump to perform an operation that is dependent on a specified state of the insulin pump. Additionally, the pump controlling device includes a processor that is operable to request a current state of the insulin pump from the insulin pump via the communications component in response to the request received from the input component. The processor is also operable to receive the current state of the insulin pump from the insulin pump via the communications component. The processor is further operable to determine whether the current state of the insulin pump matches to the specified state of the insulin pump. Moreover, the processor is operable to send a command that corresponds to the request received from the input component. The command is sent via the communications component to the insulin pump to perform the operation in response to a determination that the current state of the insulin pump matches the specified state of the insulin pump.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
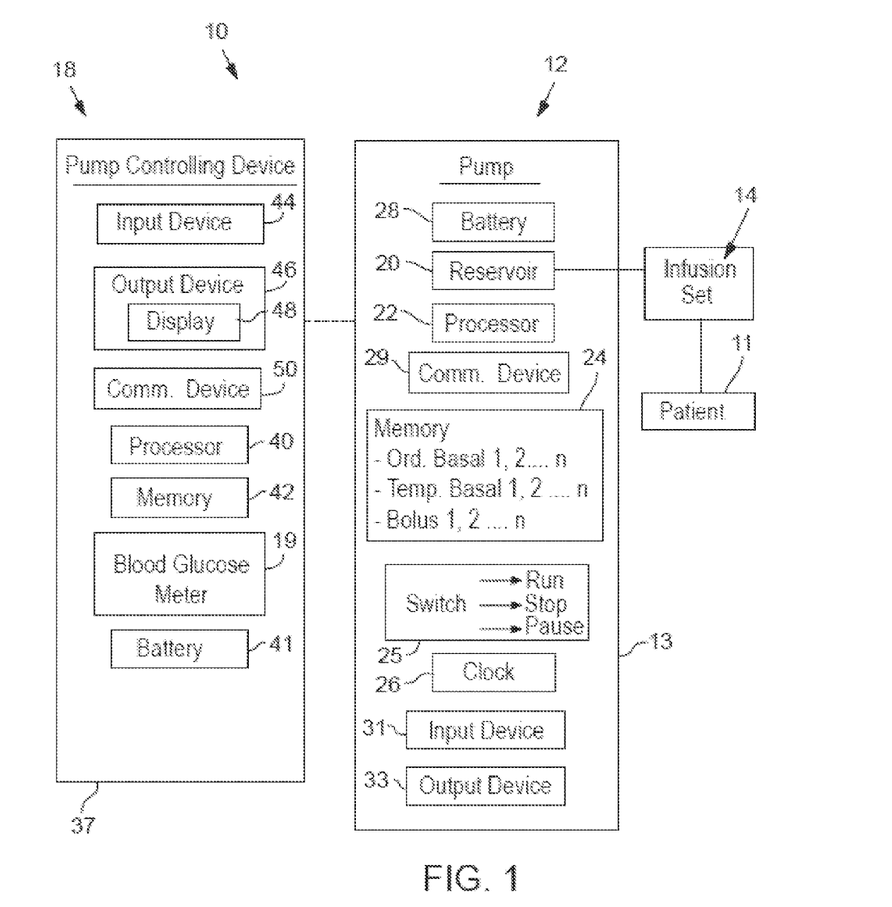
FIG. 1 is a schematic illustration of a system for delivering controlled dosages of insulin according to various exemplary embodiments of the present disclosure.
Figure 2:
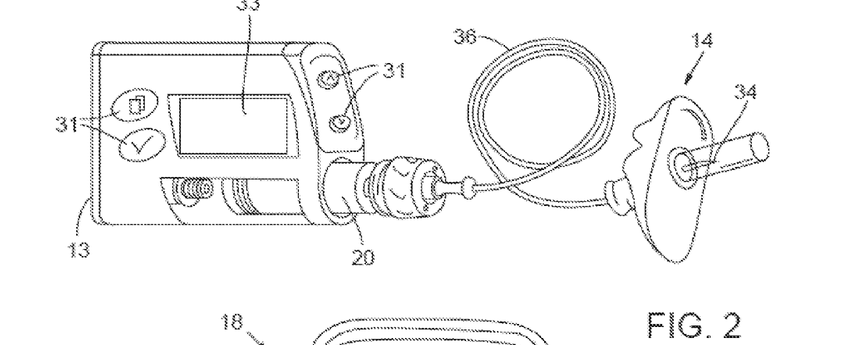
FIG. 2 is an isometric view of an insulin pump and an infusion set that can be implemented in the system of FIG. 1 according to exemplary embodiments of the present disclosure.
Figure 3:
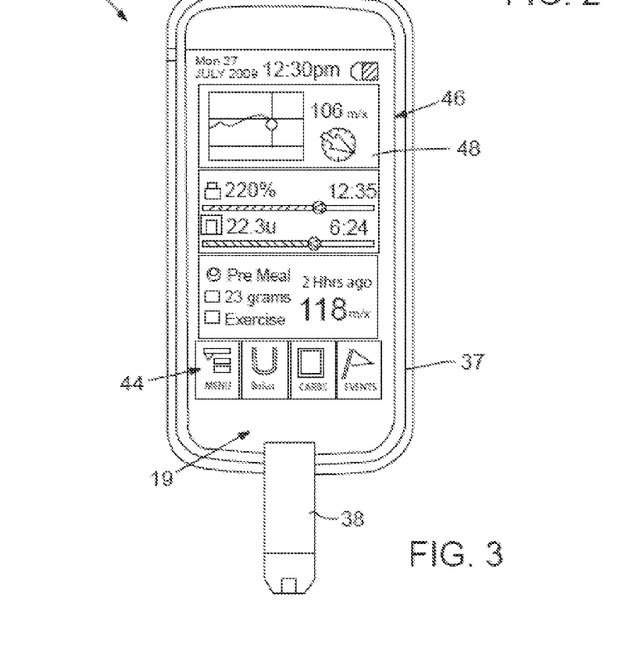
FIG. 3 is a front view of a combination blood glucose meter and pump controlling device that can be implemented in the system of FIG. 1 according to exemplary embodiments of the present disclosure.

Referring initially to FIG. 1, a system 10 for delivering controlled dosages of insulin to a patient 11 is illustrated schematically. The system 10 can generally include an insulin pump 12, an infusion set 14, and a pump controlling device 18. Exemplary embodiments of the insulin pump 12 and infusion set 14 are illustrated in FIG. 2. Also, exemplary embodiments of the pump controlling device 18 are illustrated in FIG. 3. In the embodiments shown in FIG. 3, the pump controlling device 18 is embodied on a handheld or otherwise portable blood glucose meter 19; however, the pump controlling device 18 could be separate from a blood glucose meter in some embodiments.

Referring to FIGS. 1 and 2, the insulin pump 12 can incorporate various features of a known, wearable, and portable insulin pump 12. Thus, the insulin pump 12 can include a housing 13 (FIG. 2) that supports at least one refillable reservoir 20 (i.e., insulin cartridge) containing insulin. (The reservoir 20 is shown partially removed from the housing 13 in FIG. 2.) The reservoir 20 can selectively deliver insulin to the infusion set 14 as will be described in greater detail below.

The pump 12 can also include a processor 22 (i.e., controller) that includes programmed logic and/or other elements for controlling the amount of insulin delivered from the reservoir 20, the flow rate of the insulin, the time of delivery, etc. The pump 12 can additionally include one or more memory devices 24 (FIG. 1). The memory device 24 can store application programs and data and can be constructed of any suitable combination of volatile and/or nonvolatile memory. The memory device 24 can also store one or more predefined dosage schedules (i.e., dosage "profiles") that are tailored to the particular patient. In the embodiments illustrated in FIG. 1, the different profiles are listed as "Ord. Basal 1, 2 . . . n" (i.e., ordinary basal dosage profiles), "Temp. Basal 1, 2 . . . n" (i.e., temporary basal dosage profiles), and "Bolus 1, 2 . . . n" (i.e., bolus dosage profiles). As will be discussed, the processor 22 can access these profiles stored within the memory device 24 for controlling the amount of insulin delivered, the time of delivery, the rate of delivery, etc. It will be appreciated that the memory device 24 can store any number and type of dosage profiles without departing from the scope of the present disclosure.

As shown in FIG. 1, the pump 12 can also include a switch, which is schematically illustrated and indicated at 25. The switch 25 can be used for changing the operating state of the pump 12 between two or more operating states. In the embodiments illustrated in FIG. 1, there are three operating states of the pump, RUN, STOP, and PAUSE. In the RUN mode, the pump 12 is able to deliver insulin, in the STOP mode, the pump 12 is unable to deliver insulin, and in the PAUSE mode, the pump 12 is temporarily unable to deliver insulin (e.g., due to the reservoir 20 being empty, etc.). It will be appreciated that the switch 25 can be substantially electrical (i.e., embodied as circuitry) as opposed to a mechanical switch with moving parts.

Also, the pump 12 can include a clock 26, which keeps track of the current date and time. By monitoring the clock 26, the processor 22 can track when dosages are delivered. The memory device 24 can thus save the dosage amount, the dosage type, the dosage date and time, and other data related to insulin dosages delivered by the pump 12 for future reference.

Moreover, the pump 12 can include a power source, such as a battery 28, for providing power to the components of the pump 12. The battery 28 can include a main battery that supplies power for normal operations of the pump 12, and the battery 28 can include a backup battery that supplies power for only essential operations of the pump 12 when the main battery fails. It will be appreciated that the pump 12 can include additional or alternative power sources (e.g., one or more capacitors, etc.) without departing from the scope of the present disclosure.

Additionally, the pump 12 can include one or more input components 31 that can be used by the patient 11 for inputting commands directly to the pump 12. As shown in FIG. 2, the input components 31 can include one or more buttons that the patient 11 can depress for inputting such commands. The pump 12 can further include one or more output components 33 that can output one or more messages (e.g., messages relating to dosages, etc.). In the embodiments of FIG. 2, the output component 33 includes a display screen for outputting the messages visually; however, the output component 33 could include a speaker for outputting the messages aurally. Moreover, in some embodiments, the output component can include a tactile, vibrating motor for outputting the messages in a tactile manner.

The pump 12 can further include a communications component 29. The communications component 29 can establish communications between the pump 12 and the pump controlling device 18 as will be discussed in detail below. The communications component 29 can include a wireless transceiver (e.g., BLUETOOTH™ transceiver, etc.), and/or the communications component 29 can include a connector for connecting a wire between the pump 12 and the pump controlling device 18.

Furthermore, the infusion set 14 can be of a known type. Thus, the infusion set 14 can include a cannula 34 that is inserted subcutaneously into the patient (i.e., the user, the person with diabetes, etc.). The infusion set 14 can also include a tube 36 that fluidly connects the cannula 34 to the reservoir 20 of the pump 12. As such, insulin can be delivered from the reservoir 20 and into the patient's bloodstream via the infusion set 14.

Referring now to FIGS. 1 and 3, embodiments of the pump controlling device 18 will be discussed in detail. The pump controlling device 18 can include a housing 37 that houses the components of the device 18. As shown in FIG. 1, the pump controlling device 18 can include a processor 40, which can include programmed logic and/or other elements for controlling the device 18. The device 18 can also include a memory device 42, which can store application programs and data and can be constructed of any suitable combination of volatile and/or nonvolatile memory.

Moreover, the device 18 can include a battery 41 or other power source that supplies power to the components of the device 18. Also, the device 18 can include one or more input components 44 with which the patient 11 can input commands. The input components 44 can include buttons, switches, a touch sensitive surface, or any other suitable device. The device 18 can further include one or more output components 46 that output information relating to operations of the system 10. The output components 46 can be of any suitable type, such as a display 48 that outputs information visually, a speaker that outputs audible information, a vibrating motor that outputs tactile information, etc. In the embodiments of FIG. 3, the device 18 includes the display 48, and the display 48 includes one or more touch-sensitive areas, such that the display 48 can function as both an input component 44 and an output component. Also, as shown in FIG. 3, the display 48 can display various information, such as the current date and time, graphical information about insulin dosages, etc. Furthermore, the display 48 can display user selectable options for allowing the patient 11 to enter bolus information (labeled "Bolus" in FIG. 3), carbohydrate information (labeled "Carbs" in FIG. 3), or other information related to meals, exercise, periods of stress, physiological events such as menstruation, etc. (labeled "Events" in FIG. 3).

Also, as mentioned above, the pump controlling device 18 can include a blood glucose (bG) meter 19. The meter 19 can be of a known type for detecting the current (i.e., actual) blood glucose level of the patient 11. More specifically, the patient 11 can apply blood to a test strip 38 (FIG. 3), and the meter 19 can receive the strip 38 and detect the amount of glucose in the blood thereon. This information can be useful for calculating an appropriate bolus dosage or for other purposes. Also, this information can be stored in the memory device 42 in a suitable database for future analysis.

The blood glucose readings can also be associated or otherwise stored with other information in the memory device 42. For instance, the memory device 42 can store the blood glucose readings with other health related information of the particular patient 11. More specifically, the memory device 42 can store recommended bolus and carbohydrate advice history records. The memory device 42 can further store health, carbohydrate, and blood-glucose-related variables (e.g., insulin sensitivities of the patient 11 for particular time segments of particular days of the week, etc.).

The device 18 can further include a communications component 50, such as a wireless transceiver (e.g., a BLUETOOTH™ transceiver, etc.) or a connector for connecting a wire. Thus, the communications component 50 of the pump controlling device 18 can selectively communicate with the communications component 29 of the insulin pump 12 wirelessly and/or via a hardwire connection. As will be discussed, the communication components 50, 29 can provide two-way communication between the pump controlling device 18 and the insulin pump 12.

Thus, the processor 40 can run software stored in the memory device 42. Also, various input commands can be provided from the patient 11 via the input component 44 (e.g., the touch-sensitive surface of the display 48) for performing various functions. For instance, the processor 40 can calculate a recommended meal bolus, a recommended correction bolus, a recommended total bolus, and/or a suggested carbohydrate amount in this manner. Also, the processor 40 can cause the communications component 50 to transmit various control commands to the pump 12. The pump controlling device 18 can send a variety of control commands, such as a START PUMP command, which causes the pump 12 to start pumping insulin. (As will be discussed, the START PUMP command can cause the pump 12 to adjust the switch 25 to change the pump 12 from the STOP or PAUSE state to the RUN state.) The insulin amount, dosage time, insulin flow rate, etc. can also be specified in this command. Moreover, the pump controlling device 18 can send a STOP PUMP command, which causes the pump 12 to stop pumping insulin (i.e., change from the RUN state to the STOP or PAUSE state). The pump controlling device 18 can also send other commands to the pump 12, such as commands for adjusting the current insulin delivery profile (e.g., change delivery from an ordinary basal rate to a temporary basal rate, etc.).

Figure 4:
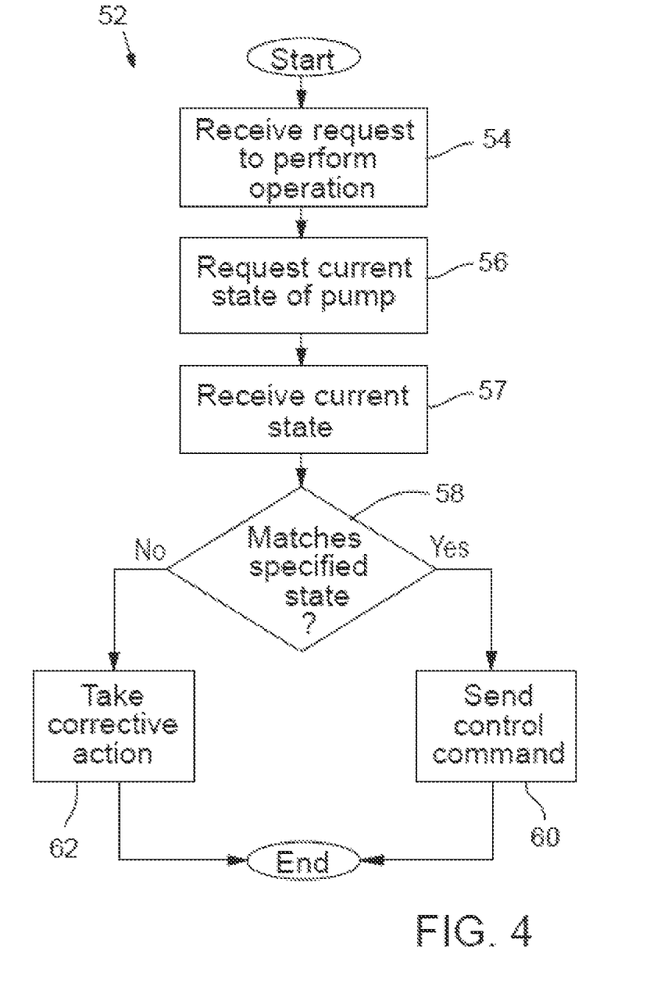
FIG. 4 is a flowchart illustrating a general method of controlling the insulin pump according to various embodiments of the present disclosure.

Referring now to FIG. 4, a method 52 of operating the system 10 is illustrated generally. As will be discussed, the method 52 dictates how the pump controlling device 18 sends control commands to the pump 12, for instance, when the patient 11 uses the pump controlling device 10 to control the pump 12. As will be discussed, initiating and completing the operation can be dependent on the pump 12 being in a specified state. For instance, starting delivery of insulin (i.e., the requested operation) can be dependent on the pump 12 currently being in the STOP or PAUSE mode (i.e., specified state). Otherwise, if the pump 12 is already in the RUN mode, and the pump control device 18 was to send a command to start insulin delivery, errors could occur. (In some embodiments, the memory device 42 of the pump controlling device 18 can store the specified states of the pump 12 necessary for performing each possible requested operation.) Thus, as will be discussed, the method 52 can ensure that the system 10 operates efficiently and accurately.

As shown, the method 52 can begin in block 54, wherein the pump controlling device 18 can receive a request from the patient 11 for the pump 12 to perform an operation. The patient 11 can supply the request using the touch-sensitive display 48 or other input components 44. The request could be of various types, such as a request to start pumping a basal or bolus dosage (discussed in detail in relation to FIG. 5) or a request to start a temporary basal dosage (discussed in relation to FIG. 6). It will be appreciated that the request could be of other types without departing from the scope of the present disclosure.

Then, in block 56, the pump controlling device 18 can request a current operating state of the pump 12 from the insulin pump 12 via paired communications between the devices 29, 50. Next, in block 57, the pump controlling device 18 can receive a signal indicating the current operating state of the pump 12 via communications between the devices 29, 50.

Subsequently, in decision block 58, the processor 40 can determine whether the current operating state of the pump 12 received in block 57 matches the specified operating state stored in the memory device 42. If the current operating state matches the specified operating state (i.e., decision block 58 answered affirmatively), then block 60 can follow, and the pump controlling device 18 can send a control command to the pump 12. Upon receiving the command, the processor 22 can output local control commands and cause the pump 12 to operate as requested by the patient 11 in block 54.

However, if the current operating state does not match the specified state (i.e., decision block 58 answered negatively), then block 62 can follow in some embodiments. In block 62, the pump controlling device 18 can take various corrective actions. In some embodiments, the pump controlling device 18 can send control commands to the pump 12, which cause the pump 12 to automatically change the configuration of the switch 25 to the specified operating state necessary for completing the operation requested by the patient 11 in block 54. Other corrective actions can be performed in block 62 without departing from the scope of the present disclosure. In additional embodiments, when the current operating state does not match the specified state (i.e., decision block answered negatively), then the output component 46 of the pump controlling device 18 outputs a message to the patient 11 (e.g., a visual warning message on the display 48). This message can inform the patient 11 that the operation requested cannot be performed, or the message can include other information.

Figure 5:
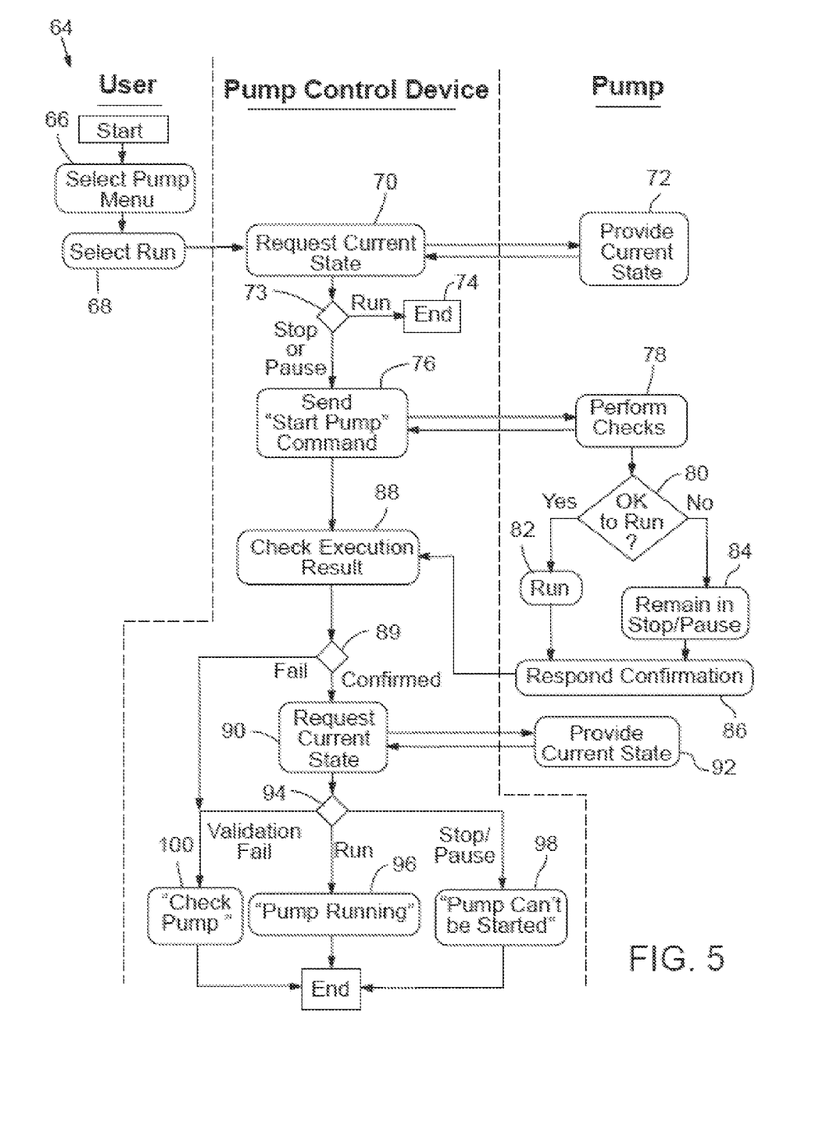
FIG. 5 is a flowchart illustrating a method of operating the system of FIG. 1 wherein a user requests that the pump start delivering insulin.

Referring now to FIG. 5, more specific embodiments of a method 64 of operating the system 10 will be discussed. As will be discussed, the system 10 can operate according to this method 64 when the patient 11 wishes to start pumping insulin with the pump 12 using the pump control device 18 as a remote controller of the pump 12. Various preconditions can be met before the method 64 initiates. For instance, the pump control device 18 and the pump 12 can be turned on; the communication components 29, 50 can be paired to allow two-way communication; etc.

The method 64 can begin in block 66, wherein the patient 11 can select a pump menu on the pump controlling device 18. More specifically, the patient 11 can use the touch-sensitive display 48 to navigate to and select a menu relating to the pump 12. The menu can display one or more selectable icons, including one icon that relates to turning on the pump 12 for insulin delivery. For example, the menu can include an icon that reads "RUN," and the patient 11 can select this icon (in block 68 of FIG. 5) when the patient 11 wishes the pump 12 to start delivering insulin.

As stated above, the memory device 42 can include a list of specified operational states of the pump 12 that are necessary for completing requested operations. In the present case, for example, the memory device 42 can indicate that the pump 12 (i.e., the switch 25) needs to be in the STOP or PAUSE operational state for the insulin pumping requested in block 68 to be started.

Thus, in block 70, the pump controlling device 18 can request the current operational state from the pump 12. Then, in block 72, the pump 12 can respond with the current operational state of the pump 12.

Next, in decision block 73, the processor 40 can compare the current operational state of the pump 12 to the specified state stored in the memory device 42. If there is no match (i.e., the current operational state is RUN, meaning that the pump 12 is already pumping insulin), then the method 64 can end in block 74. However, if there is a match between the current state and the specified state (i.e., the current operational state is either STOP or PAUSE), then block 76 can follow.

In block 76, the pump controlling device 18 can send a "Start Pump" to the pump 12 via communications between the communication components 29, 50. In some embodiments, the processor 40 can send a command to the switch 25 on the pump 12 to change from the current operational state (STOP or PAUSE) to the RUN state.

Next, in block 78, the pump 12 can perform a self-check before the pump 12 actually begins to pump insulin. For instance, the pump 12 can check the amount of insulin available in the reservoir 20 to determine if the pump 12 will be able to complete the pumping operation fully. In additional embodiments, the pump 12 can check the infusion set 14 to determine whether any occlusions exist therein before pumping. Thus, in block 80, the pump 12 can determine whether the self-check revealed any problems with starting insulin delivery. If so, then block 84 can follow, and the pump 12 can remain in the current operating state (i.e., in the STOP or PAUSE operating state). However, if the self-check revealed no problems with starting insulin delivery, then in block 82, the processor 22 can cause the switch 25 to switch to the RUN operating state. As a result, the pump 12 is now able to start delivering insulin. Specifically, the processor 22 of the pump 12 can determine the insulin dosage amount according to the day of the week, the time of day, and other considerations and according to the corresponding insulin dosage profile stored in the memory device 24. In other embodiments, the control command transmitted in block 76 can include specific dosage amounts, flow rates, and other parameters determined by the processor 40, and the pump 12 can pump insulin according to those control commands.

In block 86, a confirmation of the results of the respective block 82 or 84 can be sent from the pump 12 back to the pump control device 18. Also, in some embodiments, if the pump 12 is successfully placed in RUN mode and/or pumping has been initiated, then the output component 33 of the pump 12 can output a corresponding visual, audible, or tactile message.

Next, in block 88, the pump controlling device 18 can attempt to check the execution result of the pump 12. Then, in decision block 89, it is determined whether the execution result has been confirmed or has failed. If there is a failure, then the display 48 or other output component 46 of the pump controlling device 12 can indicate that the patient 11 needs to check the pump 12 for problems. However, if there is no failure determined in block 89, then the pump controlling device 18 can again request the current operating state of the pump 12 in block 90. In response, the pump 12 can send its current operating state back to the device 18 in block 92.

If the pump controlling device 18 determines that the pump 12 is currently running and delivering insulin, then in block 96, the display 48 or other output component 46 can output a corresponding message (e.g., display a message that the "Pump is Running"). If the pump controlling device 18 determines that the pump 12 is still in the STOP or PAUSE states, then in block 98, the display 48 or other output component 46 can output a message stating that the "Pump Cannot Be Started" or other similar message. If there is failure in communications between the pump 12 and the pump controlling device 18 and the execution result cannot be verified by the pump controlling device 18, then in block 100, the display 48 or other output component 46 can output a message stating that the pump 12 should be checked by the patient 11.

Figure 6:
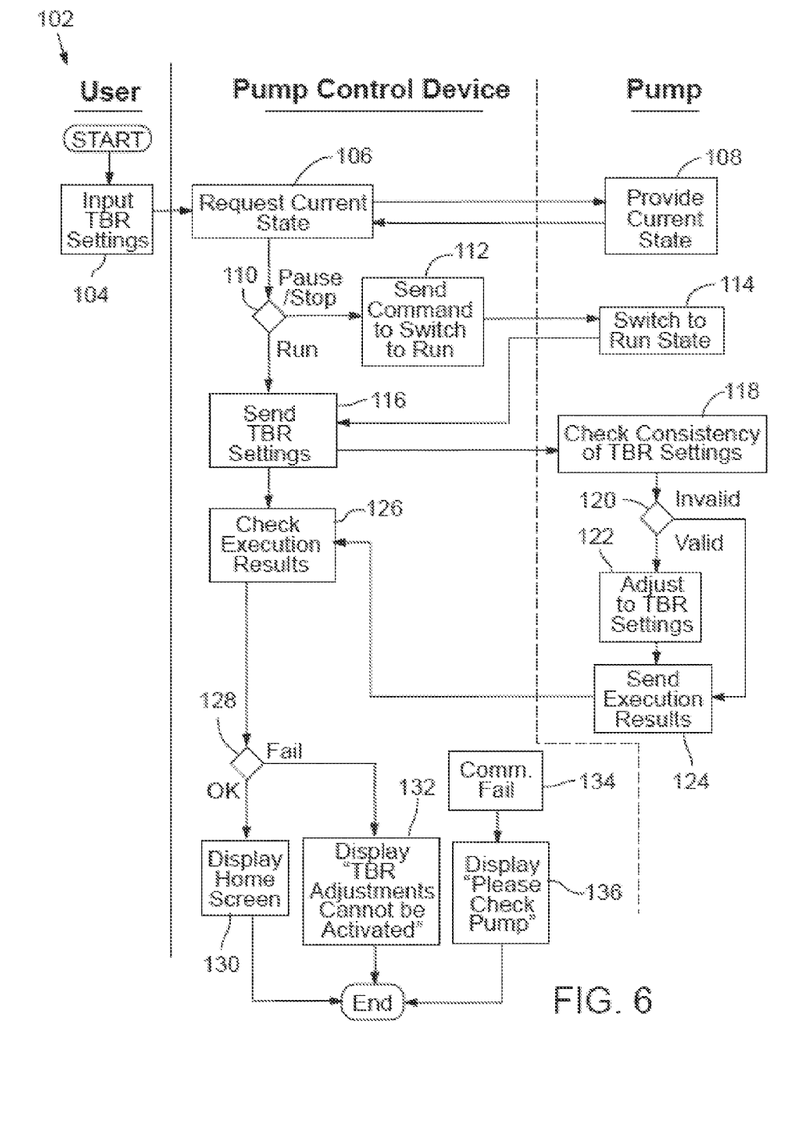
FIG. 6 is a flowchart illustrating a method of operating the system of FIG. 1 wherein a user requests that the pump begin delivery of a temporary basal dosage rate.

Referring to FIG. 6, additional embodiments of a method 102 of operating the system 10 will be discussed. In these embodiments, the patient 11 desires the pump 12 to begin delivering a temporary basal rate (TBR). In this example, it will be assumed that the pump 12 needs to be in the RUN operational state (the specified state) to deliver insulin according to the TBR.

Thus, in block 104, the patient 11 can input the temporary basal rate (TBR) settings using the input component 44 included on the pump controlling device 18. These TBR settings can be set according to various conditions such as the current day of the week, the foods that the patient 11 intends to eat during the day, etc.

Upon receiving the TBR settings, the pump controlling device 18 in block 106 can request the current operating state of the pump 12. In response, the pump 12 can send its current operational state in block 108.

Next, in decision block 110, the pump controlling device 18 can determine whether the current operating state of the pump 12 matches the specified state for delivering the requested temporary basal rate. If the current state matches the specified state (here, the pump 12 is in the RUN state), then block 116 can follow, and the pump control device 18 can send the TBR settings provided in block 104 to the pump 12. However, if the current state does not match the specified state (here, the pump 12 is in either the STOP or PAUSE state), then block 112 can follow.

In block 112, the pump controlling device 18 can take corrective action and send a control command to the pump 12 so that the switch 25 of the pump 12 changes to the RUN state in block 114. Then, block 116 can follow, and the pump control device 18 can send the TBR settings provided in block 104 to the pump 12. It will be appreciated that decision block 110, block 112, and/or block 116 can incorporate the methods discussed above with relation to FIG. 5 to ensure that the operating state of the pump 12 matches the specified state for delivering the requested temporary basal rate.

Next, in blocks 118 and 120, the pump 12 can check whether the TBR settings are consistent with the particular basal rate settings for the particular patient 11. If the TBR settings are valid, block 122 can follow, and the processor 22 can cause the TBR settings to be saved in the memory device 24 and can cause the reservoir 20 to deliver insulin according to the new TBR settings.

Then, in block 124, the pump 12 can send execution results back to the pump control device 18, and in block 126 and 128, the pump control device 18 can check those execution results. If the pump controlling device 18 determines that the pump 12 is now pumping according to the TBR settings, then block 130 can follow, and the display 48 can display a top level or "home" screen. However, if the pump controlling device 18 determines that the pump 12 is not pumping according to the TBR settings, then block 132 can follow, and the display 48 can display a message stating that the TBR adjustments cannot be activated. Moreover, if there is a communications failure between the pump controlling device 18 and the pump 12 (block 134), then block 136 can follow, and the display 48 can display a message stating that the patient 11 should check the pump 12.

It will be appreciated that the pump controlling device 18 can control the pump 12 in other ways by first checking that the current operational state of the pump 12 matches a specified state. For instance, the pump controlling device 18 can stop the pump 12 from pumping. In this case, the device 18 can first check to see that the pump 12 is in the RUN state before the device 18 attempts to send out a command to stop the pump 12 from pumping.

Accordingly, the system 10 and its method of use can ensure that the pump 12 functions effectively and efficiently. The pump controlling device 18 checks the current state of the pump 12 instead of assuming that the pump 12 is in an expected state such that the pump 12 can operate as intended. Also, the interactions between the patient 11, the pump 12, and the pump controlling device 18 can be advantageously streamlined.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The present disclosure is well suited to a wide variety of computer network systems over numerous topologies. Within this field, the configuration and management of large networks comprise storage devices and computers that are communicatively coupled to dissimilar computers and storage devices over a network, such as the Internet.

What is claimed is:

1. A computer-implemented method of operating a diabetes treatment system that includes an insulin pump and a pump controlling device that is operable to communicate with and control the insulin pump, comprising:
   receiving, by the pump controlling device, a request for the insulin pump to perform an operation that is dependent on a specified state of the pump;
   requesting, by the pump controlling device, a current state of the insulin pump from the insulin pump;
   receiving, by the pump controlling device from the insulin pump, the current state of the insulin pump;
   determining, by the pump controlling device, whether the current state of the insulin pump matches to the specified state of the insulin pump;
   sending, by the pump controlling device to the insulin pump, a command to perform the operation in response to a determination that the current state of the insulin pump matches the specified state of the insulin pump; and
   performing, by the pump controlling device, a corrective action intended to change the current state of the insulin pump, the performing in response to a determination that the current state of the insulin pump does not match the specified state of the insulin pump.

2. The method of claim 1, wherein performing the corrective action includes sending, by the pump controlling device to the insulin pump, a command to change the current state of the insulin pump to the specified state of the pump.

3. The method of claim 1, wherein the insulin pump has a run state and at least one of a pause state and a stop state, wherein the request to perform an operation is a request for the insulin pump to start insulin delivery, wherein starting insulin delivery is dependent on the insulin pump currently being in the at least one of the pause state and the stop state, wherein sending the command to start insulin delivery occurs in response to a determination that the current state of the insulin pump is the at least one of the pause state and the stop state.

4. The method of claim 1, wherein the insulin pump has a run state and at least one of a pause state and a stop state, wherein the request to perform an operation is a request for the insulin pump to activate a temporary basal rate of delivery of insulin, wherein activating the temporary basal rate is dependent on the insulin pump currently being in a run state, and wherein sending the command to activate the temporary basal rate occurs in response to a determination that the current state of the insulin pump is in the run state.

5. The method of claim 1, further comprising requesting, by the pump controlling device from the insulin pump, an execution result of sending the command to perform the operation.

6. The method of claim 5, further comprising outputting, by the pump controlling device, a message that conveys the execution result.

7. The method of claim 6, wherein outputting the message includes visually displaying the message on a display that is included on the pump controlling device.

8. A diabetes treatment system comprising:
   an insulin pump operable to selectively deliver insulin to a patient; and
   a pump controlling device with a communications component that is operable to provide two-way communication between the insulin pump and the pump controlling device, the pump controlling device also including an input component configured to receive a request for the insulin pump to perform an operation that is dependent on a specified state of the insulin pump, the pump controlling device also including a processor that is operable to request a current state of the insulin pump from the insulin pump via the communications component, the processor also operable to receive the current state of the insulin pump from the insulin pump, the processor further operable to determine whether the current state of the insulin pump matches to the specified state of the insulin pump, the processor also operable to send a command via the communications component to the insulin pump to perform the operation in response to a determination that the current state of the insulin pump matches the specified state of the insulin pump and sends a different command, via the communications component to the insulin pump, in response to a determination that the current state of the insulin pump does not match the specified state of the insulin pump, where the different command changes the current state of the insulin pump to the specified state of the pump.

9. The system of claim 8, wherein the pump controlling device also includes a memory device that stores the specified state of the insulin pump.

10. The system of claim 8, wherein the processor is further operable to request, from the insulin pump, an execution result of sending the command to perform the operation, wherein the processor is operable to receive the execution result, and wherein pump controlling device further includes an output component that is configured to output a message that conveys the execution result.

11. The system of claim 10, wherein the output component is a display that is operable to output a visual message that conveys the execution result.

12. The diabetes treatment system of claim 8 wherein the insulin pump includes a switch that controls the operating state of the insulin pump, wherein the insulin pump is configured to receive the different command from the pump controlling device and change the switch in accordance with the different command.

13. The diabetes treatment system of claim 8 wherein the state of the insulin pump is selected from a group consisting of a run state, a pause state and a stop state.

14. A pump controlling device that is operable to control an insulin pump comprising:
   a communications component that is operable to provide two-way communication with the insulin pump;

an input component configured to receive a request for the insulin pump to perform an operation that is dependent on a specified state of the insulin pump; and a processor that is operable to request a current state of the insulin pump from the insulin pump via the communications component in response to the request received from the input component, the processor also operable to receive the current state of the insulin pump from the insulin pump via the communications component, the processor further operable to determine whether the current state of the insulin pump matches to the specified state of the insulin pump, the processor also operable to send a command that corresponds to the request received from the input component, the command sent via the communications component to the insulin pump to perform the operation in response to a determination that the current state of the insulin pump matches the specified state of the insulin pump and sends a different command, via the communications component to the insulin pump, in response to a determination that the current state of the insulin pump does not match the specified state of the insulin pump, where the different command changes the current state of the insulin pump to the specified state of the pump.

15. The pump controlling device of claim 14, further including a memory device that stores the specified state of the insulin pump.

16. The pump controlling device of claim 14, wherein the processor is further operable to request, from the insulin pump, an execution result of sending the command to perform the operation, wherein the processor is operable to receive the execution result, and wherein pump controlling device further includes an output component that is configured to output a message that conveys the execution result.

17. The pump controlling device of claim 16, wherein the output component is a display that is operable to output a visual message that conveys the execution result.

18. The pump controlling device of claim 14 is interfaced with an insulin pump, wherein the insulin pump includes a switch that controls the operating state of the insulin pump, wherein the insulin pump is configured to receive the different command from the pump controlling device and change the switch in accordance with the different command.

* * * * *